US006203552B1

(12) United States Patent
Bagley et al.

(10) Patent No.: US 6,203,552 B1
(45) Date of Patent: Mar. 20, 2001

(54) MINIMALLY INVASIVE MEDICAL RETRIEVAL DEVICE

(75) Inventors: Demetrius H. Bagley, Philadelphia, PA (US); Timothy G. Vendrely, Kendallville, IN (US)

(73) Assignees: Cook Urological Incorporated, Spencer; MED Institute Inc., West Lafayette, both of IN (US)

( * ) Notice: Subject to any disclaimer, the term of this patent is extended or adjusted under 35 U.S.C. 154(b) by 0 days.

(21) Appl. No.: 09/404,874

(22) Filed: Mar. 19, 1999

Related U.S. Application Data

(60) Provisional application No. 60/078,920, filed on Mar. 20, 1998.

(51) Int. Cl.[7] ............................. A61B 17/22; A61B 17/50
(52) U.S. Cl. ............................................................ 606/127
(58) Field of Search ................................... 606/127, 128; 600/206, 210, 209

(56) References Cited

U.S. PATENT DOCUMENTS

| | | |
|---|---|---|
| 2,556,783 | 6/1951 | Wallace . |
| 4,046,150 * | 9/1977 | Schwartz et al. ............... 606/127 |
| 4,190,042 * | 2/1980 | Sinnreich ...................... 600/206 |
| 4,519,795 | 5/1985 | Hitchcock, Jr. et al. . |
| 4,590,938 | 5/1986 | Segura et al. . |
| 4,611,594 * | 9/1986 | Grayhack et al. ............... 606/127 |
| 4,682,599 * | 7/1987 | Konomura ..................... 606/127 |
| 5,176,688 * | 1/1993 | Narayan et al. ................ 606/127 |
| 5,330,482 * | 7/1994 | Gibbs et al. ................... 606/127 |
| 5,376,094 * | 12/1994 | Kline .......................... 606/127 |
| 5,397,320 * | 3/1995 | Essig et al. ................... 606/127 |
| 5,658,296 * | 8/1997 | Bates et al. ................... 606/127 |
| 5,792,145 * | 8/1998 | Bates et al. ................... 606/127 |

FOREIGN PATENT DOCUMENTS

| | | |
|---|---|---|
| 3717657 | 12/1988 | (DE) . |
| 4115136 | 12/1992 | (DE) . |
| 19722429 | 12/1998 | (DE) . |
| 9418888 | 9/1994 | (WO) . |
| 9717021 | 5/1997 | (WO) . |
| 9916365 | 4/1999 | (WO) . |

* cited by examiner

Primary Examiner—Paul J. Hirsch
(74) Attorney, Agent, or Firm—Richard J. Godlewski; James B. Hunt

(57) ABSTRACT

A minimally invasive medical retrieval device 10 useful for the removal of objects such as stones, calculi, concretions, foreign bodies and the like from the urinary, biliary, vascular or other systems includes a sheath 12 containing at least three wires 14 adjacently disposed in the sheath 12. At least one of the wires 14, and preferably all of them, can be moved longitudinally with respect to the sheath 12. The wires 14 have distal portions 16 which are formed so as to allow the engaging and removal of the object or objects. The distal portions 16 of the wires 14 preferably form a helical basket 22 or 40 particularly adapted for engaging urinary stones, calculi and concretions. Other grasping and manipulating shapes are useful as well. The wires 14 are substantially wedge-shaped in cross-section and substantially fill the entire cross-sectional area of the interior 26 of the sheath 12. The wedge-shaped wires 14 can be partly contained within a stainless steel cannula 28 positioned in the sheath 12. The sheath 12 can be of very small diameter, significantly smaller than the diameters of existing retrieval or extraction devices, preferably from about 0.5 to about 6.0 French. Unexpectedly, despite these small diameters, the baskets, graspers and the like into which the wedge-shaped wires 14 are formed simultaneously exhibit good resistance to twisting and bending, while being capable of being formed into shapes (such as helical baskets) not normally achieved with flat wires.

22 Claims, 2 Drawing Sheets

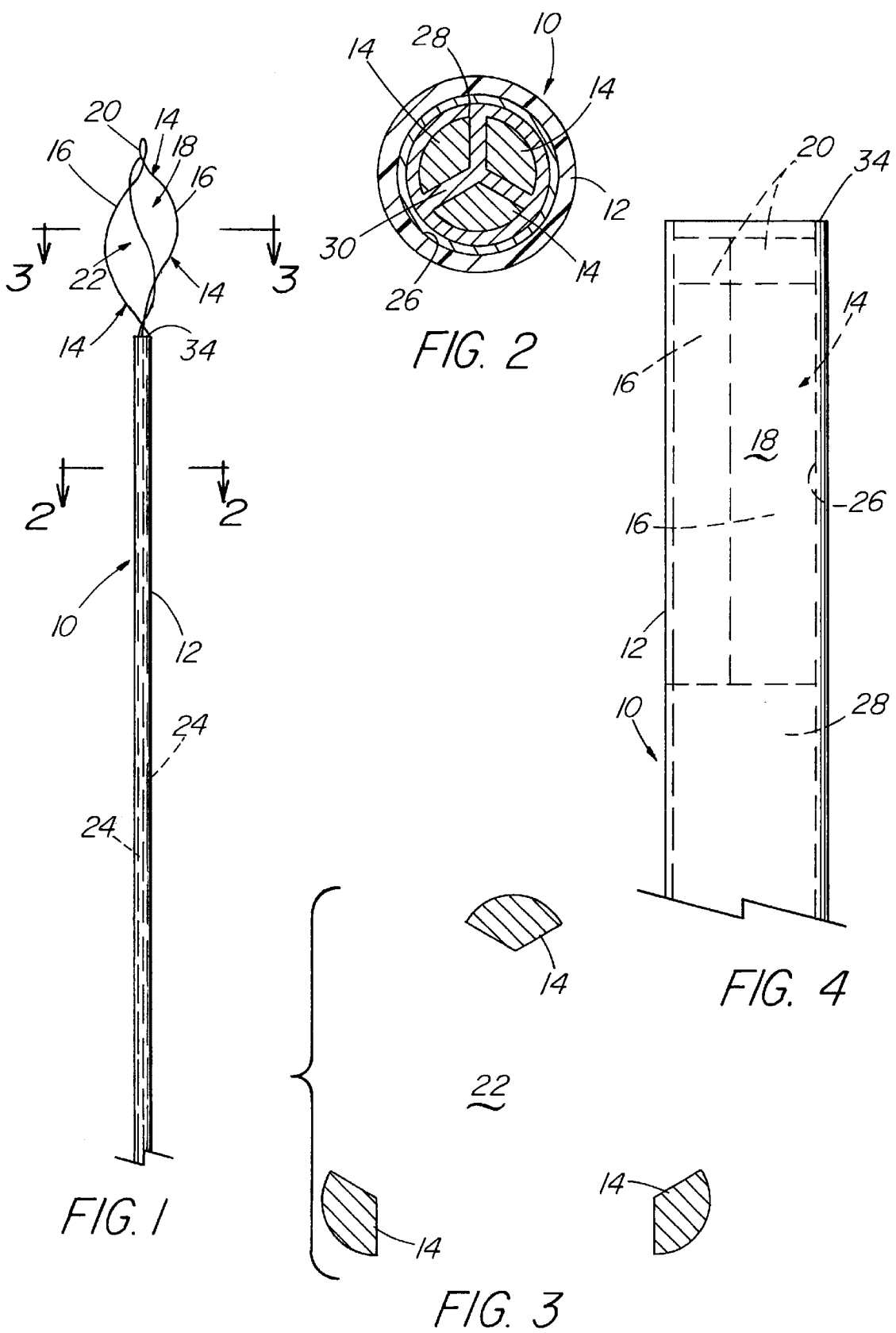

MINIMALLY INVASIVE MEDICAL RETRIEVAL DEVICE

CROSS-REFERENCE TO RELATED APPLICATIONS

This application claims priority of provisional application Ser. No. 60/078,920, filed Mar. 20, 1998.

TECHNICAL FIELD

This invention relates generally to surgical devices, and more particularly to devices for capturing and retrieving or extracting stones, calculi, concretions, foreign bodies and the like from a human or veterinary patient.

BACKGROUND OF THE INVENTION

Various organs and passages in the body are subject to the development of stones, calculi and the like. For example, gallstones are a common problem in the United States and are the most frequent cause of gallbladder inflammation. Calculi and concretions in other parts of the biliary system are also commonplace. Similarly, stones, calculi, concretions and the like can develop throughout the renal or urinary system, not only in the ureters and distal to them, but also in the renal tubules and in the major and minor renal calyxes.

Minimally invasive surgical procedures have been developed for the removal of stones, calculi, concretions and the like from the biliary and urinary systems, as well as for the removal or retrieval of foreign bodies from a variety of locations in the body. Such procedures avoid the performance of open surgical procedures such as, for example, a cholecystectomy. Minimally invasive procedures can instead employ percutaneous access, in which stones, calculi, concretions, foreign bodies and the like are removed through a percutaneously inserted access sheath. Several access routes are suitable, depending upon the specific system and the particular location in the system at which the stones, calculi, concretions, foreign bodies or the like are found.

Without regard to the particular access route, percutaneous extraction is often based upon the use of catheters or similar devices to engage and remove the stones, calculi, concretions, foreign bodies and the like. Such catheters and devices typically comprise a hollow, flexible sheath and a plurality of round or flat wires positioned in but extendable from the sheath. The wires are joined or arranged so as to form a means such as a basket or forceps for engaging the object to be retrieved, when the wires are extended from the sheath. The engagement means (for example, the basket) can be collapsed by withdrawing the wires into the sheath. A helical basket permits entry of the stone or the like from the side of the basket, while an open ended ("eggwhip") basket allows a head-on approach to the stone or the like. Other retrievers and graspers can include forceps or can include a loop or snare for encircling the body to be removed, the loop or snare being made of the round or flat wire.

Despite their successful use for some time, retrieval devices including round or flat wire baskets are subject to some drawbacks. It is believed, for example, that helical stone extractor baskets have never been successfully produced with flat wires, but only with round wires. Flat wires, however, have the advantage that baskets incorporating them exhibit better resistance to twisting during use. Moreover, while surgical techniques have advanced, and endoscope accessory channels of relatively smaller diameter have been developed, efforts to reduce the diameter of round wires incorporated in stone extraction baskets have unfortunately not met with similar success. In practice, the lowest useful round wire diameter (even with stainless steel wire) remains about 0.007 to 0.010 in. (about 0.178 to 0.254 mm). Because there is a significant amount of wasted space inside any sheath or cannula containing round or flat wires, this limit on useful wire diameter has prevented the development of useful helical stone extractors of small diameter, and in particular, of extractors having an outside diameter (that is, the diameter of the sheath or cannula containing the wires) below about 1.7 French (0.022 in. or 0.56 mm). The development of retrieval devices having smaller diameters than this, especially diameters below 1 French, would allow the removal of stones, calculi, concretions, foreign bodies and the like from locations deeper in the body than can be achieved with these larger, existing devices.

It should therefore be clear that it would be highly desirable to have a device for the capture and retrieval or extraction of stones, calculi, concretions, foreign bodies and the like which had an overall outside diameter significantly smaller than the outside diameter of existing retrieval or extraction devices. It would also be highly desirable for such a device to include a basket or grasper whose wires exhibited the good resistance to twisting and bending that is enjoyed by flat wires, while being capable of being formed and maintained in a helical-shape like round wires, or in a straight, flower shape like flat wires. Additionally, a portion of helical basket, or straight, flower-shaped basket wedge-shaped wires could form a grasper. It would be particularly desirable to have such a device with an outside diameter below 1 French, even as small as 0.5 French, which retained acceptable basket strength and acceptable capture and removal, extraction or retrieval properties.

SUMMARY OF THE INVENTION

The foregoing problems are solved and a technical advance is achieved in an illustrative extraction or retrieval device which is particularly useful for capturing and extracting, retrieving or removing objects such as stones, calculi, concretions, foreign bodies and the like from a variety of locations in the body. The device of the present invention is most simply characterized in a wire assembly for insertion into the interior of a sheath, the wire assembly including at least three wires for adjacent disposition within the sheath so as to substantially fill the cross-sectional area of the sheath in which the wires are disposed.

Preferably, the wires are substantially wedge shaped, which advantageously replace the round- or flat-shaped wires of prior extraction or retrieval devices. When a wire is said to be substantially wedge-shaped, it can be considered as being a segment part with straight or curved sides, which may or may not meet at a point. The wires within a sheath or tubular member, collectively assume an approximately cylindrical form to substantially fill the sheath or member. The wires can all be of a substantially wedge-shaped form or they can be of various shapes with maybe only one wire being approximately wedge-shaped. Wires adjacent to that wedge-shaped wire should preferably conform in shape so that there is a minimum of unoccupied space in the sheath or member. It is preferred that each of the wires is substantially wedge-shaped. When the wires have curved sides and no point, the spaces can be used for accommodating debris and removing it safely. Unexpectedly, the wedge-shaped wires used in the present invention possess a combination of the useful properties of both round- and flat-shaped wires, and retain this good combination of properties even when the overall diameter of the extraction or retrieval device is significantly smaller than is possible when round or flat wires are included.

The present invention is particularly advantageous over the prior art in that the device can have an overall outside diameter significantly smaller than the outside diameter of existing retrieval or extraction devices. The retrieval device of the present invention can have an outside diameter as small as 0.5 French. This is less than one-third of the current practical lower limit of a diameter of about 1.7 French, and plainly is expected to allow the capture and extraction, removal and/or retrieval of stones, calculi, concretions, foreign bodies and the like from locations in the body much deeper than can be achieved with existing devices. Despite this small diameter, the basket or grasper formed from the wedge-shaped wires simultaneously exhibit the good resistance to twisting and bending that is enjoyed by flat wires, while being capable of being formed and maintained in a helical shape like round wires or flat wires. Additionally, a portion of the helical, straight, or flower shaped basket with the substantially wedge-shaped wires can form a grasper.

The device of the present invention enjoys acceptable basket strength and acceptable capture and retrieval properties, even at such dramatically reduced overall diameters. It should go without saying that the smaller diameter is also expected to reduce the risk of patient discomfort and the risk of inadvertent damage to tissue during introduction and manipulation of the device in the patient.

The retrieval device of the present invention finds use in a wide range of procedures, particularly in minimally invasive procedures. Accordingly, while the preferred embodiment of the device is a retriever or extractor for urological procedures, the present invention is also expected to be useful in biliary procedures, in vascular procedures and in the retrieval of foreign objects from a variety of body cavities. Moreover, while it is preferred the distal ends of the wedge-shaped wires are formed into a helical basket, the invention encompasses the forming of the wires into a wide variety of other conventional grasping or capture structures.

In a first aspect, the minimally invasive medical retrieval device comprises a wire assembly for insertion into a sheath, the assembly including at least three wires for adjacent disposition within the sheath. At least one of the wires is longitudinally movable with respect to the sheath, and each wire has a distal portion, which together form a means such as a basket for engaging and permitting the removal of an object from the patient. The sheath has an interior with a defined cross-sectional area, and the wires substantially fill the cross-sectional area of the interior of the sheath. Preferably, at least one of the wires have a wedge shape, and the sides of the wedge-shaped wire conforms to the sides of the adjacent wires. The device further includes a sheath having an interior for adjacent disposition for the at least three wires therein. "Adjacent" means that the at least three wires lie side by side and are preferably parallel to one another, but are not coaxial with one another; that is, their axes are not coincident. "Object" is used in a very broad sense and includes kidney stones, renal and urinary calculi and concretions, gallstones, biliary calculi and concretions, foreign objects such as fragments of previously implanted medical devices (for example, cardiac and pacemaker leads in the vascular system), and the like. To achieve this end, the distal ends of the wires are joined together so that the engaging means formed by them comprises a basket capable of capturing the object or objects. More preferably, the basket is helical in shape.

In another aspect, the medical retrieval device comprises a sheath and at least three wires adjacently disposed within the sheath. At least one of the wires is longitudinally movable with respect to the sheath, and the at least three wires have distal portions, which together form a means such as a basket for engaging or permitting removal of an object from a patient. At least one of the wires of the retrieval device is substantially wedge-shaped, and conforms the shape of adjacent wires to substantially fill the cross-sectional area of the sheath.

The first two aspects of the present invention preferably comprises three to six of the wedge shaped wires, and more preferably three of them. Also preferably, the sheath has an interior with a defined cross-sectional area, and the at least three wires substantially fill the cross-sectional area of the interior of the sheath. "Substantially" means that, for a given cross-sectional area filled by the material making up the at least three wires, the at least three wires are capable of fitting into a circle of smaller diameter than would the same number of circular wires possessing the same cross-sectional area filled by the same material. "Substantially" more preferably means that a small amount of space can be left between the wires, and/or between the wires and the sheath, to facilitate the particular use intended for the device. For example, some minimal room is required to permit one or more of the wires to slide with respect to the sheath, and some minimal room is required to permit the wires to be secured together proximal of the engaging means. A single wire folded over on itself and having two portions positioned in the sheath is equivalent to two separate wires, and should be considered as two separate wires for the purposes of the present invention. Preferably, the sheath is about 0.5 French to about 6.0 French in diameter, and more preferably about 1.7 to about 3.0 French in diameter.

The wires can be composed of stainless steel, nitinol or a polymer composite. "Polymer composite" includes a polymer or plastic material having a fibrous or particulate filler incorporated in it. While not excluded by the invention, polymeric and plastic materials by themselves are generally expected to lack the strength necessary to function in the range of sizes preferred for the practice of the invention. This expectation applies to even the stiffer polyimide/polyamide materials.

The first two aspects of the invention can also include a cannula positioned in the sheath, partly containing or attached the at least three wires. The cannula is composed of a medical grade material suitable to the performance of the particular minimally invasive retrieval to be performed. Most conveniently, the cannula is composed of stainless steel. When the at least three wires are intended to move in unison with respect to the sheath, it is preferred that the wires are secured together proximal of the engaging means partway along their length, for example, by solder disposed between each of the individual wires, and between the individual wires and the cannula.

In a third aspect, the present invention is directed to a device of the type disclosed above, comprising a specific combination of such elements. In particular, in its third aspect the present invention is directed to a minimally invasive medical retrieval device for removing an object from within a patient, comprising a sheath; three to six wedge-shaped wires adjacently disposed within the sheath, at least one of the wires being longitudinally movable with respect to the cannula, and the wires each having distal portions which together form a helical basket, or a straight, flower shaped basket, or an open helical, or straight flower shaped structure for capturing and permitting the removal of the object from the patient; and a cannula positioned in the sheath, partly containing the wedge-shaped wires; wherein the sheath has an interior with a defined cross-sectional area, and the wedge-shaped wires substantially fill the cross-sectional area of the interior of the sheath; wherein the wires are composed of stainless steel or nitinol, and are secured together proximal of the helical basket by solder extending partway along their length, disposed between each of the individual wedge-shaped wires, and between the wedge-shaped wires and the cannula; and wherein the sheath is about 0.5 French to about 6.0 French in diameter.

In a final aspect, the present invention is directed to a minimally invasive medical retrieval device for removing an object from within a patient, comprising a sheath, and at least three wires adjacently disposed within the sheath, at least one of the at least three wires being longitudinally movable with respect to the cannula, and the at least three wires each having distal portions which together form a means for engaging and permitting the removal of the object from the patient, wherein the sheath has an interior with a defined cross-sectional area, and the at least three wires substantially fill the cross-sectional area of the interior of the sheath. This third aspect of the present invention can also include the various elements above. In this aspect of the invention, the wires need not be wedge-shaped, but can have any cross-section which fills the sheath and thereby minimizes the cross-section of the retrieval device. However, it should be noted that "adjacently," as defined above, necessarily excludes from any of these three aspects of the invention an arrangement in which the wires are hollow and disposed coaxially with one another.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is a cross-sectional view taken along line 2—2 of FIG. 1;

FIG. 3 is a cross-sectional view taken along line 3—3 of FIG. 1;

FIG. 4 is another perspective view of the preferred embodiment of the present invention;

DETAILED DESCRIPTION

Figure 5:
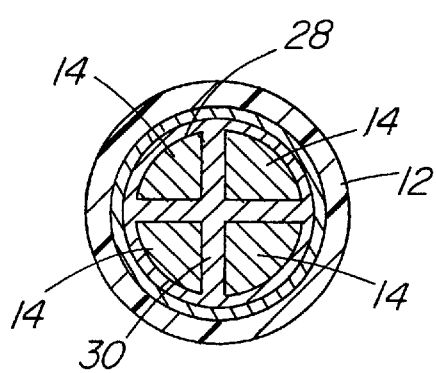
FIG. 5 is a cross-sectional view of another preferred embodiment of the present invention, similar to FIG. 2.

With reference first to FIGS. 1 through 3, a minimally invasive medical retrieval device 10 according to the present invention for removing an object from a patient is thereshown. The retrieval device 10 first comprises an outer sheath (preferably flexible), sleeve, tube, catheter, cannula or the like, any and all of these being generally represented by a sheath 12. The sheath 12 has an interior 26 of defined cross-sectional area. The sheath 12 can be composed of any medical grade material suitable for use at the location in the body from which an object is to be removed. The construction of sheath and the like in general is well known in the art, and further details relating to the structure of the sheath 12 need not be given here, particularly since such structure will depend upon the use to which the retrieval device 10 will be put. However, the retrieval device 10 can further comprise a conventional introducer sheath (not shown) to facilitate introduction of the sheath 12 into the body of the patient.

The retrieval device 10 next comprises a wire assembly including at least three wires 14 adjacently disposed in the interior 26 of the sheath 12. The wires 14 each have a distal portion 16, and the distal portions 16 of the wires 14 together form a means 18 for engaging and permitting removal of an object from a patient. At least one and preferably all of the wires 14 are longitudinally movable with respect to the sheath 12 so that the engaging means 18 can be extended from the sheath 12 after introduction of the sheath 12 into the patient (FIG. 4). The wires 14 can be composed of any medical grade material having a flexibility and strength suitable for introduction to the site from which an object is to be retrieved, and suitable for secure grasping, containment and/or removal of the object. The wires 14 are preferably composed of a metal such as stainless steel or nitinol (the latter being preferably in a superelastic state). However, the wires 14 can also be composed of synthetic materials of suitable strength, such as polymeric or plastic materials having fibrous or particulate fillers incorporated in them. Such synthetic materials are examples of polymer composites useful in the invention. It should be noted that, although not excluded from use in the invention, polymeric and plastic materials lacking such fillers are probably not preferred for use in the invention; it is believed that they generally lack the strength necessary to function adequately in the range of diameters preferred in the practice of the present invention. This is believed to be true even of relatively stiff materials, such as the polyimides/polyamides.

The retrieval device 10 of the present invention can be characterized in two ways. First, the present invention can be characterized in that the wires 14 substantially fill the cross-sectional area of the interior 26 of the sheath 12, "substantially" having the meaning given above. Such substantial filling packs as much solid material as possible into the cross-sectional profile of the sheath 12 and results in the sheath 12 possessing the minimum diameter possible for the amount of material used in the wires 14. In this first characterization of the invention, the cross-sectional shape of the wires 14 is not critical to the practice of the invention; however, it is preferred that the wires 14 each be wedge-shaped or pie-shaped in cross-section. Other shapes, particularly shapes which can longitudinally slide freely with respect to one another, are also expected to be useful in the invention, so long as the cross-sectional area of the interior 26 of the sheath 12 remains substantially filled.

Alternatively, the present invention can be characterized in that the wires 14 are each wedge-shaped or pie-shaped in cross-section, again minimizing the cross-sectional profile of the sheath 12. When a wire is said to be substantially wedge-shaped, it can be considered as being a segment part with straight or curved sides which may or may not meet at a point. The wires collectively within a sheath or tubular member, assume an approximately cylindrical form to substantially fill the sheath or member. The wires can all be of a substantially wedge shaped form or they can be of various shapes with maybe only one wire being approximately wedge shaped. Wires adjacent to that wedge-shaped wire should preferably conform in shape so that there is a minimum of unoccupied space in the member.

Figure 9:
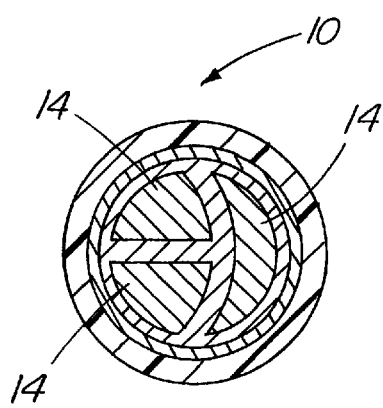
FIG. 9 is a cross-sectional view of another preferred embodiment of the present invention similar to FIG. 2 in which the wedge-shaped wires are depicted with other than just straight sides.
Figure 6:
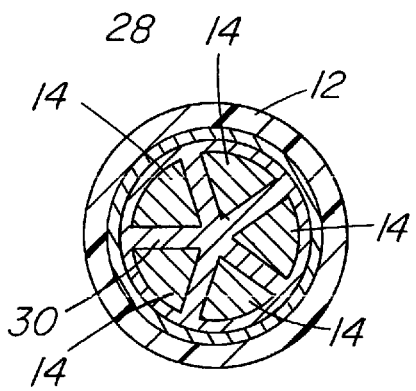
FIG. 6 is a cross-sectional view of another preferred embodiment of the present invention, similar to FIG. 2.
Figure 7:
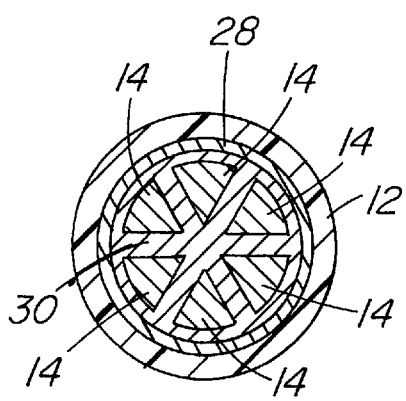
FIG. 7 is a cross-sectional view of another preferred embodiment of the present invention, similar to FIG. 2.

FIG. 9 depicts a cross-sectional view of another preferred embodiment of the present invention similar to FIG. 2 in which the wedge-shaped wires 14 are other than with just straight sides. This form of device 10 has wedge-shaped wires in which the sides thereof can take any curvilinear and/or straight configuration. The wires can also be inwardly or outwardly tapered. However, it is preferred that each of the wires is substantially wedge-shaped. When the wires have curved sides and no point, the spaces can be used for accommodating debris and removing it safely.

Preferably, the retrieval device 10 of the present invention includes from three to six of the wires 14. Cross-sectional views of devices having three, four, five and six wires 14 are shown in FIGS. 2, 5, 6 and 7, respectively. Because the wedge-shaped wires 14 used in the present invention are generally not commercially available, for cost savings it is highly preferred that the individual ones of the wires 14 used in a single retrieval device 10 are identical to one another, that is, they each have the same apex angle. However, the invention certainly contemplates the use of wires of different apex angles in a single retrieval device 10, if such different wires would yield an engaging means 18 having particularly useful properties.

Three identical wires 14 provide for a particularly preferred construction of the retrieval device 10, because they can be formed into an engaging means 18 having particular usefulness in retrieving stones and calculi from the urinary system. More particularly, as shown in FIG. 1, in this first preferred embodiment of the present invention, the distal portions 16 of each of the wires 14 are joined together in such a manner so that the engaging means 18 formed by them comprises an open-ended helical basket 22. Such joining is most simply carried out by twisting the very tips 20 of each of the wires 14 together, allowing the open-ended helical basket 22 to be particularly shaped for the capture of urinary stones and calculi. The twisted wire tips 20 can be very short.

Figure 8:
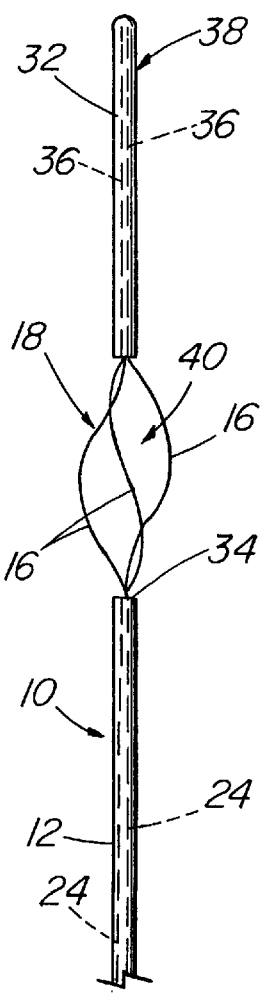
FIG. 8 is a perspective view of another preferred embodiment of the present invention.

Alternatively, in another preferred embodiment of the present invention, as shown in FIG. 8 the engaging means 18 can instead comprise a side-entry helical basket 40, formed between the portions 24 of the wires proximal to the engaging means 18, and end portions 36 of the wires 14 distal to the engaging means 18. The distal end portions 36 of the wires 14 are covered with a segment 38 of the material of which the sheath 12 is composed, so that the retrieval device 10 is provided with an atraumatic extended tip 32 distal of the engaging means 18 (the basket 40), the tip 32 being comprised of the distal wire portions 36 and the cover segment 38. The side-entry helical basket 40 can be withdrawn into the interior 26 of the sheath 12 by proximal withdrawal of the wedge-shaped wires 14 until the extended tip 32 abuts the distal end 34 of the sheath 12.

Without regard to the particular arrangement of the wires 14, however, the helical shapes of the baskets 22 and 40 are retained during use despite the relatively small diameter of the wedge-shaped wires 14, because the wires 14 unexpectedly exhibit the good resistance to twisting and bending that is enjoyed by previously known flat wires.

Of course, the same or other numbers of wires 14 can be used to form other engaging means 18, such as graspers, forceps, dislodgers and the like. Moreover, the present invention encompasses embodiments in which the engaging means is actuated by independent movement of the wires 14 with respect to one another. The arrangement of such embodiments should be evident to those skilled in the art without further description, in view of the present disclosure. However, and particularly when embodied in a retriever for urinary stones and calculi, it is preferred that the wires 14 of the retrieval device 10 are secured together at some location proximal of the engaging means 18, so as to move in unison with respect to one another. The portions or segments 24 of the wires 14 proximal of the engaging means 18 can be partly contained in a cannula 28 positioned in the interior 26 of the sheath 12. The cannula 28 is preferably composed of stainless steel, although other suitable medical grade materials can be used as well. The wires 14 are secured to each other and to the cannula 28 by an adhesive or by solder 30 applied to the proximal portions or segments 24 of the wires 14, disposed between the individual ones of the wires 14, and between the wires 14 and the cannula 28. Such securement provides a useful amount of stiffness to the retrieval device 10 proximal of the engaging means 18. The adhesive or the solder 30 should of course not extend as far as the engaging means 18 and thereby prevent it from opening when extended from the sheath 12.

The retrieval device 10 of the present invention is most advantageous over prior devices in that the close packing of the wires 14 in the sheath 12 allows the sheath 12 (and the engaging means 18 in it) to have an overall diameter which is significantly smaller than the overall diameters of the prior devices. The diameter of the sheath 12 is preferably from about 0.5 to about 6.0 French, and more preferably, from about 1.7 to about 3.0 French. Even at sizes which can be contained in these small diameters, the wedge-shaped wires 14 still behave more like flat wires than round ones, with respect to their resistance to bending and twisting. Such resistance unexpectedly provides the engaging means 18 formed from the wedge-shaped wires 14 with good utility.

Use of the retrieval device 10 of the present invention should be readily apparent to those skilled in the art, and no extensive explanation of such use is necessary herein. In the conventional fashion, the sheath 12 (containing the engaging means 18, as shown in FIG. 4) is positioned in the patient with its distal end 34 near the object to be retrieved. A conventional introducer sheath, not shown, can be used to facilitate such positioning. At least one and preferably all of the wires 14 are then moved longitudinally with respect to the sheath 12 so as to extend the engaging means 18 from the sheath 12 (FIG. 1), and the engaging means 18 then used to manipulate, capture, contain, grasp or otherwise allow the removal or retrieval of the object from the patient. The specific details of the use of the engaging means 18 will of course depend upon its particular structure, and again, those skilled in the art should be well aware of such details, without requiring their repetition here. It is also contemplated that the ends of the wires distal remain unconnected so as to produce an open ended basket or grasper.

The retrieval device 10 of the present invention should be composed of medical grade materials which can be sterilized by conventional procedures prior to use. Conveniently, the retrieval device 10 can be made of relatively inexpensive synthetic and metallic materials, so that the device 10 can be disposed of after a single use, rather than being resterilized and reused. Such reuse, however, is also contemplated within the scope of the invention.

Of course, these and the other details of construction can be changed to adapt the retrieval device 10 of the present invention to the particular surgical technique to be performed.

It should be clear from the foregoing disclosure that the retrieval device 10 of the present invention is particularly advantageous over prior devices in a variety of ways. Most importantly, the present invention is particularly advantageous over the prior art in that the device (and in particular, its outer sheath) can have an overall outside diameter significantly smaller than the outside diameter of existing retrieval or extraction devices. Indeed, the retrieval device of the present invention can have an outside diameter as small as 0.5 French. The retrieval device of the present invention is expected to allow the capture and removal, extraction and/or retrieval of stones, calculi, concretions, foreign bodies and the like from locations in the body much deeper than can be achieved with existing devices. The basket, grasper or other engagement means formed from the wedge-shaped wires enjoys the good resistance to twisting and bending possessed by flat wires, despite this small diameter, and as noted in the preferred embodiment of the invention is capable of being formed and maintained in a helical shape, just like round wires. The retrieval device of the present invention enjoys good capture and retrieval properties, as well as good basket strength, even at an overall diameter less than one-third of that of the smallest conventional device. The smaller overall diameters enjoyed by the present invention should also reduce the risk of patient trauma during use.

As noted above, the retrieval device of the present invention is expected to find use in a wide variety of procedures, including urological procedures, biliary procedures, vascular procedures and procedures for the retrieval of foreign objects from a variety of body cavities. Moreover, while the description of the preferred embodiment of the invention includes a helical basket as a specific example of an engagement means, the present invention is plainly not limited to the use of a helical basket as a means for engaging stones, calculi, concretions, foreign bodies and the like. Other engagement means which can be formed from wedge-shaped wires of the present invention should be immediately apparent to those skilled in the art, in light of the present disclosure. In particular, the wedge-shaped wires can be formed into a basket, grasper, forceps or the like which includes cut away portions to facilitate the capture, grasping or holding of the object to be engaged and retrieved.

The details of the construction or composition of the various elements of the retrieval device 10 not otherwise disclosed are not believed to be critical to the achievement of the advantages of the present invention, so long as the elements possess the strength or flexibility needed for them to perform as disclosed. The selection of any such details of construction are believed to be well within the ability of one of even rudimentary skills in this area, in view of the present disclosure.

Industrial Applicability

The present invention is useful in the performance of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A minimally invasive medical retrieval device (10) for removing an object from within a patient, comprising:
    a wire assembly for insertion in a sheath (12), the wire assembly including at least three wires (14) for adjacent disposition within the sheath (12), at least one of the at least three wires (14) being longitudinally movable with respect to the sheath (12), and the at least three wires (14) each having distal portions (16) which together form a means (18) for engaging and permitting the removal of the object from the patient;
    wherein the sheath (12) has an interior (26) with a defined cross-sectional area, and the at least three wires (14) can substantially fill the cross-sectional area of the interior (26) of the sheath (12).

2. The device (10) according to claim 1, wherein at least one of the at least three wires (14) is substantially wedge-shaped, and wherein the sides of the or each wedge-shaped wire conform to the sides of adjacent ones of the at least three wires (14).

3. The device (10) according to claim 1, wherein the device (10) further includes a sheath (12) having an interior (26) for adjacent disposition of the at least three wires (14) therein.

4. The device (10) according to claim 1 wherein the at least three wires are of noncircular cross-section.

5. The device (10) according to claim 1 wherein at least a portion of the distal portions of the at least three wires are unjoined to each other.

6. The device (10) according to claim 1, wherein the distal portions (16) of the at least three wires (14) are joined together so that the engaging means (18) formed by the at least three wires (14) comprises a basket (22 or 40) capable of capturing the object.

7. The device (10) according to claim 6, wherein the basket (22 or 40) is helical in shape.

8. The device (10) according to claim 1, further comprising from three to six of the at least three wires (14).

9. The device (10) according to claim 1, wherein the at least three wires (14) are composed of stainless steel, nitinol or a polymer composite.

10. The device (10) according to claim 1, further comprising a cannula (28) positioned in the sheath (12), at least partly contacting the at least three wires (14).

11. The device (10) according to claim 10, wherein the at least three wires (14) are secured together proximal of the engaging means (18) by solder (30) extending partway along their length, disposed between the individual ones of the at least three wires (14), and between the at least three wires (14) and the cannula (28).

12. A minimally invasive medical retrieval device (10) for removing an object from within a patient, comprising:
    a sheath (12); and
    at least three wires (14) adjacently disposed within the sheath (12), at least one of the at least three wires (14) being longitudinally movable with respect to the sheath (12) and the at least three wires (14) having distal portions (16) which together form a means (18) for engaging and permitting the removal of the object from the patient;
    wherein at least one of the wires (14) is substantially wedge-shaped, and conforms to the shape of adjacent wires to substantially fill the cross-sectional area of the sheath (12).

13. The device (10) according to claim 12, wherein the distal portions (16) of the at least three wires (14) are joined together so that the engaging means (18) formed by the at least three wires (14) comprises a basket (22 or 40) capable of capturing the object.

14. The device (10) according to claim 13, wherein the basket (22 or 40) is helical in shape.

15. The device (10) according to claim 12, wherein the distal wires are open ended, whereby the device becomes a helical, straight, or flower-shaped grasper.

16. The device (10) according to claim 12, further comprising from three to six of the at least three wires (14).

17. The device (10) according to claim 12, wherein the at least three wires (14) are composed of stainless steel, nitinol or a polymer composite.

18. The device (10) according to claim 12, further comprising a cannula (28) positioned in the sheath (12), at least partly contacting the at least three wires (14).

19. The device (10) according to claim 18, wherein the at least three wires (14) are secured together proximal of the engaging means (18) by solder (30) extending partway along their length, disposed between the individual ones of the at least three wires (14), and between the at least three wires (14) and the cannula (28).

20. The device (10) according to claim 12, wherein the at least three wires (14) are secured together proximal of the engaging means (18).

21. The device (10) according to claim 12, wherein the sheath (12) is about 0.5 French to about 6.0 French in diameter.

22. A minimally invasive medical retrieval device (10) for removing an object from within a patient, comprising:

a sheath (12);

three to six wedge-shaped wires (14) adjacently disposed within the sheath (12), at least one of the wires (14) being longitudinally movable with respect to the sheath (12), and the wires (14) each having distal portions (16) which together form a helical basket (22 or 40) for capturing and permitting the removal of the object from the patient; and a cannula (28) positioned in the sheath (12), partly containing the wedge-shaped wires (14);

wherein the sheath (12) has an interior (26) with a defined cross-sectional area, and the wedge-shaped wires (14) substantially fill the cross-sectional area of the interior (26) of the sheath (12);

wherein the wires (14) are composed of stainless steel or nitinol, and are secured together proximal of the helical basket (22) by solder (30) extending partway along their length, disposed between each of the individual wedge-shaped wires (14), and between the wedge-shaped wires (14) and the cannula (28); and wherein the sheath (12) is about 0.5 French to about 6.0 French in diameter.

* * * * *